United States Patent [19]

Avery

[11] 4,311,792
[45] Jan. 19, 1982

[54] CULTURE COLLECTING AND TRANSPORTING UNIT

[75] Inventor: Carl F. Avery, Rockford, Ill.

[73] Assignee: Marion Health and Safety, Inc., Rockford, Ill.

[21] Appl. No.: 139,771

[22] Filed: Apr. 14, 1980

[51] Int. Cl.³ .......................................... C12Q 1/24
[52] U.S. Cl. ................................. 435/30; 15/144 B; 128/759; 206/205; 206/207; 206/219; 206/569; 435/295
[58] Field of Search ................. 128/759; 435/30, 294, 435/295; 206/205, 207, 219, 569; 15/144 B

[56] References Cited

U.S. PATENT DOCUMENTS

| | | | |
|---|---|---|---|
| 1,138,244 | 5/1915 | Parker | 15/144 B |
| 2,984,852 | 5/1961 | George | 15/144 B |
| 3,450,129 | 6/1969 | Avery et al. | 128/759 |
| 3,712,296 | 1/1973 | Gradone | 128/759 |
| 4,184,483 | 1/1980 | Greenspan | 435/295 X |

Primary Examiner—Robert J. Warden
Attorney, Agent, or Firm—Leydig, Voit, Osann, Mayer & Holt, Ltd.

[57] ABSTRACT

A culture collecting swabbing tip is carried on one end portion of a small diameter flexible wire which enables the tip to reach into a curved and narrow body passage. A sleeve-type handle is telescoped slidably onto the other end portion of the wire and enables the effective length of the wire to be adjusted so that the wire can fit into an outer transport tube but can be effectively lengthened to reach into a long body passage. The transport tube contains a glass ampoule which may be broken to moisten the swabbing tip with a culture-sustaining transport media after a culture has been collected on the tip.

5 Claims, 8 Drawing Figures

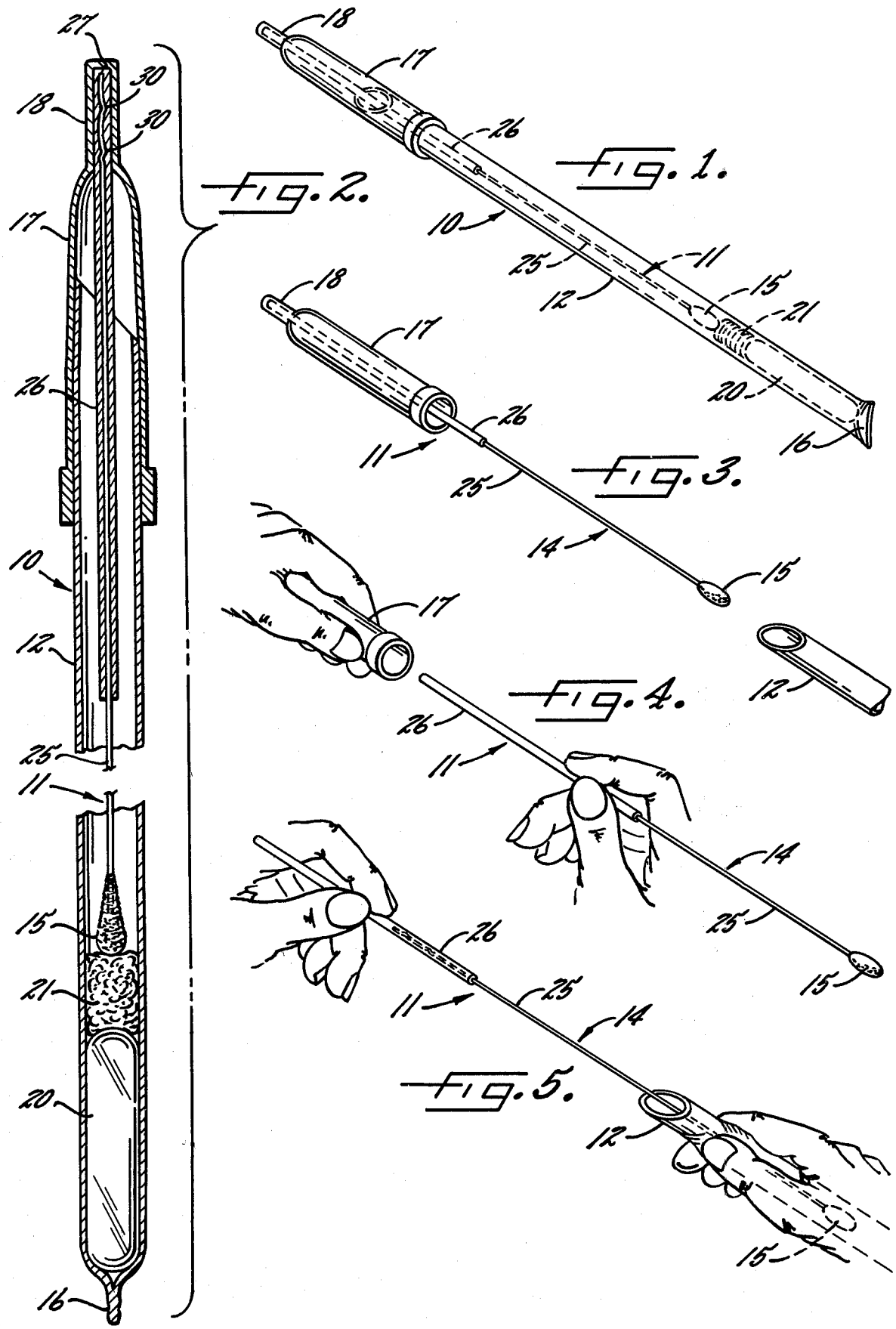

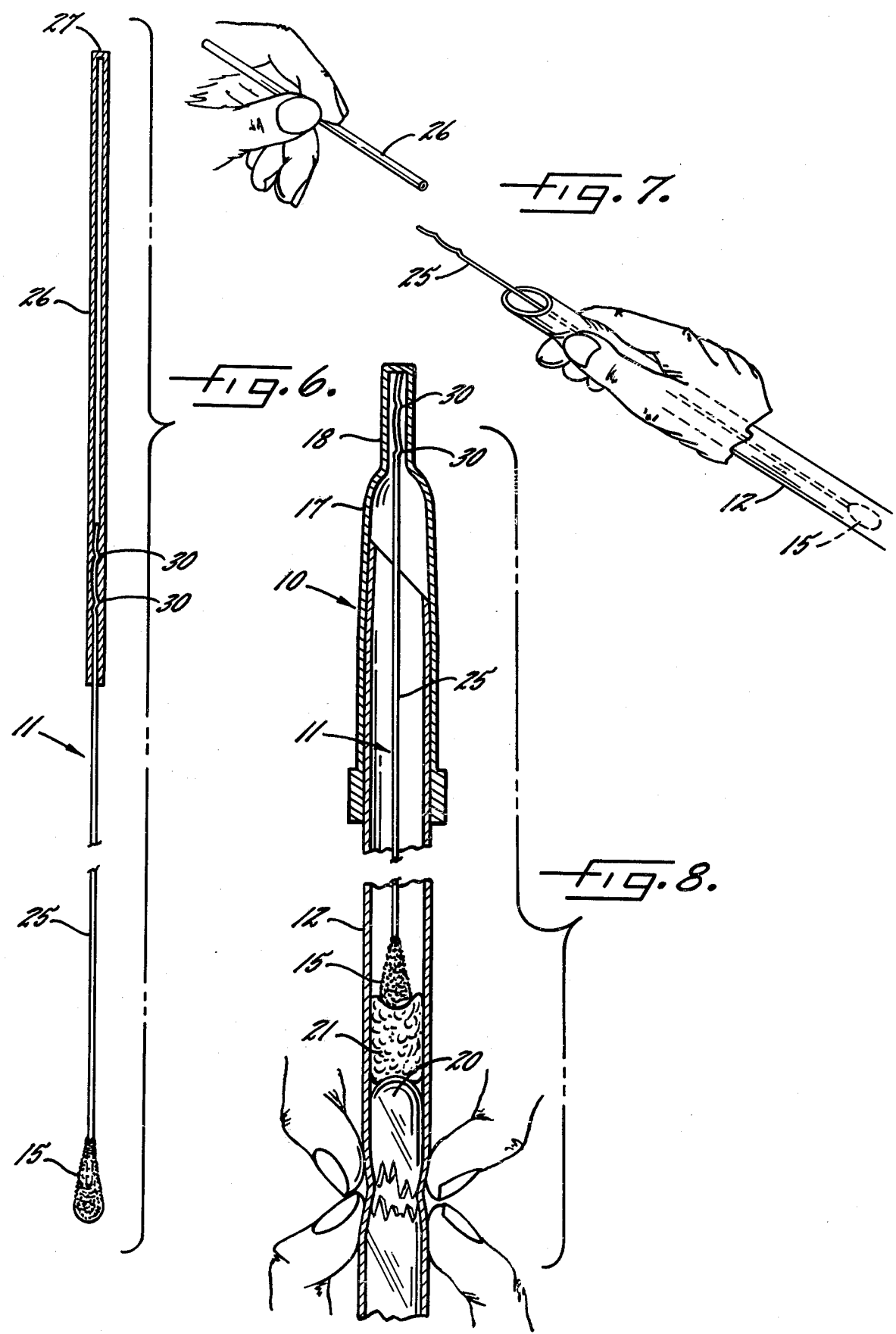

CULTURE COLLECTING AND TRANSPORTING UNIT

BACKGROUND OF THE INVENTION

This invention relates to swabs used by physicians and the like for collecting a culture from a particular area of a patient's body and for keeping the culture alive for a period of time after it has been collected. Such swabs customarily include an absorbent swabbing tip carried on the end of an elongated stem. The culture is collected by holding the stem and by swabbing a particular body area with the absorbent tip.

Many culture collecting swabs are packaged with a transport container having its own supply of culture-sustaining media. After the culture has been collected, the swab is placed into the container with the swabbing tip in contact with the media so as to keep the culture alive until it is transported to a laboratory for testing.

One of the most commercially successful culture collecting and transporting units is disclosed in Avery et al U.S. Pat. No. 3,450,129. Such a unit includes a flexible outer tube within which is contained a frangible glass ampoule having a liquid culture-sustaining media sealed therein. After the culture has been collected by a swab, the latter is placed in the tube and the tube then is squeezed to break the ampoule and release the liquid. The liquid moistens an absorbent plug which is disposed within the tube in engagement with the tip of the swab so as to keep the tip moist until the culture is transported and tested. A cap is placed over the tube to keep the inside of the tube in a substantially sterile condition during transport.

The stem of the swab disclosed in the Avery et al patent is relatively stiff and rigid and is of relatively large diameter. As a result, the swab is not capable of being used to collect cultures from curved and narrow body passages such as nasal passages or the genitourinary tract.

A swab which is capable of entering curved and narrow body passages is marketed under the trademark CALGISWAB by Inolex Corporation of Glenwood, Illinois. The tip of such a swab is carried on a stem which is in the form of a flexible wire having a relatively small diameter. As a result, the stem may be threaded into and will conform with a curved and narrow body passage to permit the swabbing tip to collect a culture from such passage.

SUMMARY OF THE INVENTION

The general aim of the present invention is to provide a new and improved self-contained culture collecting and transporting unit which retains virtually all of the attributes and advantages of the prior Avery et al unit and which is characterized by the provision of a unique swab of the flexible wire type.

A more detailed object is to provide a flexible wire swab which may be adjusted in effective length so as to enable the swab to fit within an outer transport tube of standard length while at the same time enabling the swab to be made sufficiently long to collect a culture from a long body passage.

Still another object is to provide a flexible wire swab whose effective length may be adjusted manually without contaminating either the wire or the swabbing tip.

In a more detailed sense, the invention resides in the provision of a flexible wire swab having a slidable sleeve-type handle which enables the effective length of the swab to be adjusted.

The invention also resides in the unique method of manipulating the wire, the handle and the transport tube to permit adjustment of the length of the wire without contaminating the wire.

These and other objects and advantages of the invention will become more apparent from the following detailed description when taken in conjunction with the accompanying drawings.

BRIEF DESCRIPTION OF THE DRAWINGS

FIG. 1 is a perspective view of a new and improved culture collecting and transporting unit which incorporates the unique features of the present invention.

FIG. 2 is an enlarged cross-sectional view of the unit shown in FIG. 1.

FIGS. 3, 4 and 5 are perspective views showing successive steps which may be followed preparatory to collecting a culture with the swab.

FIG. 6 is a side elevational view showing the swab after the effective length of the wire has been increased, parts of the swab being broken away and shown in section.

FIG. 7 is a perspective view showing the step of returning the swab to the transport tube.

FIG. 8 is a view similar to FIG. 2 but shows the unit after the swab has been returned to the transport tube.

DETAILED DESCRIPTION OF THE PREFERRED EMBODIMENT

As shown in the drawings for purposes of illustration, the invention is embodied in a unit 10 whose components are used for collecting a bacterial specimen or culture from a patient's body and for maintaining the culture in a live condition until such time as it can be transported to a laboratory and tested. In general, the unit comprises a swab 11 for collecting the culture and further comprises a tube 12 for holding the swab both before and after the culture is collected.

The swab 11 comprises an elongated stem 14 (FIG. 3) whose inner end carries an absorbent swabbing tip 15 upon which the culture is collected. In the present instance, the swabbing tip is made from calcium alginate but other soft and absorbent materials may be used for the tip.

Herein, the tube 12 is made of a flexible but self-sustaining plastic. The inner end of the tube is closed off by a heat seal 16 while the outer end of the tube is open. A tubular plastic cap 17 is adapted to telescope snugly but slidably over the outer end portion of the tube to close the tube both before and after the swab 11 is used. At its outer end, the cap is formed with a reduced diameter tubular neck 18 which is adapted to telescopically receive the outer end portion of the stem 14 of the swab 11 with a snug but slidable fit. When the cap is first removed from the tube, the outer end portion of the stem remains telescoped in the neck and thus the swab is pulled out of the tube as the cap is removed. In some instances, the cap is used as a handle for the swab when the culture is taken.

Disposed within the inner end portion of the tube 12 and located adjacent the heat seal 16 is a sealed ampoule 20 made of a frangible material such as glass. The ampoule is filled with a liquid culture-sustaining transport media. In the present instance, the ampoule contains modified Stuart's transport media.

The ampoule 20 is held in the lower end portion of the tube 12 by an absorbent plug 21 which is made of cotton-like material. The plug is telescoped tightly into the tube and engages the end of the ampoule. When the swab 11 is in the tube, the tip 15 contacts the plug.

When the collecting and transporting unit 10 is shipped from the manufacturer, the swab 11 is disposed within the tube 12 and is positioned with the tip 15 in engagement with the plug 21 as shown in FIGS. 1 and 2. The cap 17 is telescoped over the outer end of the tube and is located such that the outer end portion of the stem 14 is snugly received in the neck 18. The assembled unit is packaged within a substantially flat envelope (not shown) made of glassine or other suitable material which enables the unit to be sterilized by autoclaving or the like after the unit has been sealed in the envelope. Accordingly, the entire unit is maintained in a sterile condition until such time as the envelope is opened.

To collect a culture, the cap 17 is removed from the tube 12 and, as an incident thereto, the swab 11 is pulled out of the tube. A particular body passage of the patient then is swabbed with the tip 15 to obtain a culture. Thereafter, the swab and the cap are returned to the tube with the tip of the swab being positioned in contact with the plug 21. The tube then is squeezed or pinched adjacent the ampoule 20 (see FIG. 8) to break the ampoule and release the liquid therein. The liquid moistens the plug 21 which, in turn, moistens the tip 15 to keep the culture in a live condition until it reaches a laboratory for testing.

As described thus far, the culture collecting and transporting unit 10 is substantially the same as that disclosed in the aforementioned Avery et al patent. Units of the type disclosed in the Avery et al patent have been manufactured and sold for several years by the assignee of the present invention and have enjoyed significant commercial success.

In accordance with the invention, the tube 12, the cap 17, the ampoule 20 and the plug 21 of the present collecting and transporting unit 10 are virtually identical to the corresponding elements of the previously sold units but the swab 11 is uniquely modified to enable a culture to be collected from a curved and narrow passage such as a nasal passage or a passage in the genitourinary tract. Moreover, the swab is adjustable in length so that it can fit within the tube and yet can be lengthened if necessary to enable the tip 15 to reach into a very long body passage. The length adjustment may be achieved without the physician destroying the effective sterility of the swab with his fingers.

More specifically, the stem 14 of the swab 11 is made in part from a length of flexible wire 25 having a small diameter. In the present instance, the stem is formed by a six inch length of round aluminum wire having a diameter of about 0.030 inches. The wire can be easily flexed to a desired shape and tends to conform to and follow a curved body passage. This, together with the small diameter of the wire, enables the swabbing tip 15 to be threaded into a curved and very narrow body passage.

In carrying out the invention, a sleeve 26 is telescoped slidably over the outer end portion of the wire 25 and forms a handle for the wire. In addition, the sleeve 26 forms part of the stem 14 and enables the effective length of the stem to be adjusted.

Herein, the sleeve 26 consists of a cylindrical tube of transparent plastic having an inside diameter of about 0.035 inches and an outside diameter of about 0.080 inches. The extreme outer end of the sleeve is sealed closed as indicated at 27 in FIGS. 2 and 6.

In the assembled unit 10, the outer end portion of the sleeve 26 is telescoped snugly but slidably into the neck 18 of the cap 17 while the inner end portion of the sleeve is similarly telescoped over the outer end portion of the wire 25 (see FIG. 2). To insure that there is a snug fit between the sleeve and the wire, two V-shaped bends or dimples 30 are formed in the extreme outer end portion of the wire and frictionally engage the inside of the sleeve. The dimples compensate for variances in the manufacturing tolerances of the wire and the sleeve.

The outer end portion of the sleeve 26 is received within the neck 18 of the cap 17 while the inner end portion of the sleeve projects inwardly about one inch from the inner end portion of the cap in the assembled unit 10. In addition, the closed outer end 27 of the sleeve abuts the extreme outer end of the wire 25 as shown in FIG. 2. Under these conditions, the tip 15 is disposed in contact with the plug 21.

To use the unit 10, the cap 17 is removed from the tube 12. Because the sleeve 26 fits snugly with both the neck 18 and the wire 25, the swab 11 is pulled out of the tube when the cap is removed (see FIG. 3).

If the body passage which is to be swabbed is relatively short, the physician may simply leave the cap 17 on the sleeve 26 and may use the cap itself as a handle when swabbing the passage. The sleeve provides some rigidity to the outer end portion of the wire 25 and enables the physician to maintain good control over the wire and the tip 15.

After the culture has been taken from a short body passage, the physician returns the swab 11 and the cap 17 to the tube 12 and then breaks the ampoule 20 by squeezing on the tube. The culture-sustaining liquid thus is released and moistens the plug 21 and the tip 15.

If the body passage is long, the physician may grasp the cap 17 in one hand (see FIG. 4) and grasp the inwardly projecting portion of the sleeve 26 in his other hand and pull the cap completely off of the sleeve. The physician then may place the swab partially within the tube 12 as shown in FIG. 5 and squeeze inwardly on the upper end portion of the tube to pinch the wire 25 between the inside walls of the tube. By maintaining the pinch with one hand, the physician may grasp the sleeve 26 with his other hand and slide the sleeve outwardly along the wire. This exposes more of the outer end portion of the wire and effectively lengthens the wire to enable a longer body passage to be swabbed (see FIG. 6). By pinching the wire with the tube, the physician does not touch the wire with his fingers as he slides the sleeve outwardly along the wire and thus the wire is not contaminated by the physician's fingers.

After the culture has been taken, the swab 11 again is placed partially in the tube 12. The physician then again squeezes inwardly on the upper end portion of the tube to pinch and hold the wire 25 and, while the wire is being pinched, the physician pulls the sleeve 26 completely off of the wire and discards the sleeve (see FIG. 7). In this way, the sleeve which has been touched by the physician's fingers is thrown away rather than being returned to the tube and thus contamination within the tube is avoided.

After the sleeve 26 has been discarded, the cap 17 is placed onto the tube 12 and, as an incident thereto, the closed end of the neck 18 engages the outer end of the wire 25. As the cap is pushed onto the tube, the wire is moved inwardly to place the tip 15 in engagement with the plug 21 as shown in FIG. 8. The ampoule 20 then is broken by squeezing the tube.

From the foregoing, it will be apparent that the present invention brings to the art a new and improved culture collecting and transporting unit 10 having a swab 11 whose stem 14 is formed partially by a flexible wire 25 which enables the swabbing of curved and narrow body passages. The slidable sleeve 26 uniquely coacts with the wire 25, the cap 17 and the tube 12 to enable good control to be maintained over the wire and to enable the effective length of the wire to be adjusted without contaminating those parts of the swab which are returned to the tube. Many of the components of the present unit 10 are similar to those of the previously sold unit and thus presently existing equipment and procedures can be used for manufacturing and assembling those components.

I claim:

1. A culture collecting and transporting unit comprising a tube made of self-sustaining but flexible material, said tube having an open outer end and a closed inner end, a transport media located within said tube, a cap telescoped removably with the open end portion of said tube and adapted to close said tube, and a culture collecting device located within said tube, said unit being characterized in that said culture collecting device comprises an elongated flexible wire, a swabbing tip on the inner end portion of said wire and located adjacent said transport media, and a sleeve telescoped slidably over the outer end portion of said wire and telescoped slidably into said cap, said sleeve being of such length that the inner end portion of said sleeve projects inwardly from the inner end of said cap and into the outer end portion of said tube when said cap is telescoped to a fully closed position on said tube.

2. A culture collecting and transporting unit as defined in claim 1 in which the outer end of said sleeve is closed, the outer end of said wire normally abutting the closed outer end of said sleeve.

3. A culture collecting and transporting unit as defined in claim 2 further including a bend formed in the outer end portion of said wire and frictionally engaging the inside of said sleeve to restrict sliding of said sleeve along said wire.

4. A culture collecting and transporting unit as defined in claim 1 in which said sleeve is telescoped snugly over said wire and into said cap whereby said sleeve and said wire are pulled outwardly of said tube when said cap is removed from said tube.

5. A method of using the culture collecting and transporting unit defined in claim 4, said method comprising the steps of, manually grasping said tube and said cap and pulling said cap away from said tube, grasping said sleeve and said cap and pulling said cap off of said sleeve, pinching said tube into grasping engagement with said wire while pulling on said sleeve to slide said sleeve outwardly along said wire, removing said device from said tube, collecting a culture on said swabbing tip and replacing said device in said tube all while holding said sleeve, pinching said tube into grasping engagement with said wire while pulling on said sleeve and sliding said sleeve outwardly off of said wire, and replacing said cap on said tube.

* * * * *